United States Patent [19]
Grimes

[11] Patent Number: 5,176,711
[45] Date of Patent: Jan. 5, 1993

[54] ACETABULAR REVISION SYSTEM

[76] Inventor: James B. Grimes, 1921 18th St., Bakersfield, Calif. 93301

[21] Appl. No.: 665,118

[22] Filed: Mar. 6, 1991

[51] Int. Cl.⁵ .............................................. A61F 2/34
[52] U.S. Cl. ........................................ 623/22; 623/18
[58] Field of Search ...................... 623/22, 23, 18, 19; 606/91, 60

[56] References Cited

U.S. PATENT DOCUMENTS

| | | | |
|---|---|---|---|
| 2,765,787 | 10/1956 | Pellett . | |
| 3,740,769 | 6/1973 | Haboush . | |
| 3,803,641 | 4/1974 | Golyakhovsky | 623/19 |
| 3,896,504 | 7/1975 | Fischer | 623/22 |
| 4,040,131 | 8/1977 | Gristina | 623/19 |
| 4,042,980 | 8/1977 | Swanson et al. | 623/19 X |
| 4,045,826 | 9/1977 | Stroot | 623/19 |
| 4,245,360 | 1/1981 | Brinckmann et al. | 623/22 |
| 4,792,337 | 12/1988 | Müller | 623/22 |
| 4,828,565 | 5/1989 | Duthoit et al. | 623/22 |
| 4,919,669 | 4/1990 | Lannelongue | 623/19 |
| 4,919,672 | 4/1990 | Millar et al. | 623/22 |
| 4,923,473 | 5/1990 | Griss et al. | 623/22 |
| 4,959,072 | 9/1990 | Morscher et al. | 623/22 |

FOREIGN PATENT DOCUMENTS

| | | | |
|---|---|---|---|
| 0241361 | 10/1987 | European Pat. Off. . | |
| 0328847 | 8/1989 | European Pat. Off. | 623/22 |
| 2621667 | 11/1977 | Fed. Rep. of Germany | 623/18 |
| 3205527 | 8/1983 | Fed. Rep. of Germany | 623/22 |
| 2387641 | 12/1978 | France | 623/22 |
| 2578162 | 9/1986 | France | 623/22 |
| 2595241 | 9/1987 | France . | |
| 0749392 | 7/1980 | U.S.S.R. | 623/19 |
| 8801491 | 3/1988 | World Int. Prop. O. | 623/22 |

OTHER PUBLICATIONS

Author: Syntex Laboratories; Title: Bulk Femoral Head Allografts Exhibit High Rate of Failure; Jul./Aug. 1991; pp. 1 & 5.

Author: Mulroy et al.; Title: Failure to Acetabular Autogenous Grafts in Total Hip Arthroplasty; Dec. 1990; pp. 1536-1540.

Primary Examiner—Randall L. Green
Assistant Examiner—D. Willse
Attorney, Agent, or Firm—Senniger, Powers, Leavitt & Roedel

[57] ABSTRACT

An implantable acetabular hip prosthesis includes a primary shell having an outer surface adapted to be received within a surgically prepared acetabulum, and an inner cavity for receiving a bearing insert which, in turn, receives a femoral head portion of a femoral component of a total hip prosthesis. The acetabular component of the prosthesis further includes an augmentation piece which is attachable to the primary shell and which fills a defect, such as a rim or cavitary defect, adjacent the natural acetabulum. The augmentation piece may be fixedly retained in a selected one of a plurality of angular orientations, relative to the primary shell. A plurality of augmentation pieces of varying sizes and shapes may be provided to allow the orthopedic surgeon to select an appropriate augmentation piece to match the defect.

26 Claims, 8 Drawing Sheets

ACETABULAR REVISION SYSTEM

BACKGROUND AND SUMMARY OF THE INVENTION

This invention relates generally to an implantable acetabular hip prosthesis, and more particularly to an implantable acetabular hip prosthesis which is well-suited for use in revision surgery or in other circumstances in which a void, such as a rim or cavitary defect, is present in the bony structure surrounding the natural acetabulum.

Total hip arthroplasty is a well-known and recognized procedure. A typical procedure involves replacing the top portion of the femur, including the head of the femur which serves as the "ball" in the ball-and-socket hip joint. Replacement of the socket is typically accomplished by cementing or otherwise fixing in a surgically prepared natural socket (the acetabulum) a substantially hemispherical cup or shell which is designed to receive the ballshaped head of the femoral prosthesis component. Fixation of the acetabular component within the surgically prepared natural acetabulum is vital to the long-term success of the procedure, and is typically accomplished by use of bone cement, bone screws, bone ingrowth processes, or a combination of these and/or other techniques.

A particular problem which orthopedic surgeons sometimes face in implantation of the acetabular component of a total hip prosthesis is the presence of a void or defect, such as a rim or cavitary defect, in the superior and superior/posterior acetabular region. Such voids or defects may be caused by superior or superior/posterior migration of a previously implanted acetabular prosthesis. Migration may also occur in situations in which a bipolar acetabular component has been implanted. Developmental problems (e.g., congenital dysplasia of the hip) may also produce voids or defects in the acetabular area. Natural deterioration of the bony tissue surrounding the acetabulum may also occur due to natural processes, such as infections, and/or trauma. Orthopedic surgeons presently use large segments of cadaveric bone graft in conjunction with known substantially hemispherical prosthesis components to reconstruct the acetabulum of a patient in which such voids or defects are present. However, this approach can be relatively time consuming and expensive, and does not always achieve desired and lasting results. Other attempts to address this problem, including the use of oblong acetabular components or alternative positioning of hemispherical components, have been made, but with only limited or mixed success.

It is an object of the present invention to provide an implantable acetabular hip prosthesis which is well-suited for use in the reconstruction of a natural acetabulum in which a superior or superior/posterior void or defect is present.

It is another object of the present invention to provide an implantable hip prosthesis which is particularly well-suited for use in the reconstruction of a natural acetabulum in which a superior or superior/posterior void or defect is present, and which is modular in design so as to allow the surgeon greater introoperative flexibility to properly reconstruct an acetabulum in which such a void or defect is present so that the center of motion of the hip prosthesis is very nearly the same as the normal center of motion of the hip.

These and other objects are achieved in an implantable acetabular hip prosthesis which comprises a primary shell having an outer surface adapted to be received within a surgically prepared acetabulum, and having an inner cavity for receiving a bearing insert which, in turn, receives a femoral head portion of a femoral component of a total hip prosthesis. The acetabular prosthesis further comprises an augmentation means, attachable to the primary shell, for filling a superior or superior/posterior defect, such as a rim or cavitary defect, adjacent the surgically prepared acetabulum. In one embodiment, the augmentation means comprises an augmentation piece, means for attaching the augmentation piece to the primary shell so as to allow the augmentation piece to be angularly (i.e., rotatably) adjusted relative to the shell, and means for fixedly retaining the augmentation piece in a selected angular orientation. The augmentation piece may comprise a partial sphere having a first surface adapted for implantation adjacent the bony tissue of the ilium (i.e., adjacent the surgically prepared periphery of the defect), a second surface adapted for disposition adjacent the outer surface of the primary shell, and a third surface which faces outwardly from the ilium when the hip prosthesis is positioned within the acetabulum. A plurality of holes extend from the third surface to the first surface for receiving bone screws to fasten the augmentation piece to the surrounding tissue. The third surface is provided with a recess to improve access to at least one of these screws.

In one embodiment of the hip prosthesis of the present invention, the means for attaching the augmentation piece to the primary shell, and for fixedly retaining the augmentation piece in a selected or desired angular orientation, comprises a Morse taper arrangement (which serves as the primary means of fixation) and a threaded screw located along a common axis which extends through the primary shell and the augmentation piece. The Morse taper arrangement preferably comprises a male Morse taper formed on the augmentation piece, and a mating female Morse taper formed in the primary shell. The head of the screw means is received within a recess formed within the inner cavity of the primary shell, and the body of the screw extends along the common axis through the Morse taper to engage threads which are formed in a threaded opening in the augmentation piece. The common axis preferably extends through the shell and the augmentation piece at an angle of approximately 45° relative to the polar axis of the shell. In one embodiment of the invention, at least a portion of the outer surface of the primary shell and a portion of the third surface of the augmentation piece are porous coated to promote fixation to the adjacent bone by bone ingrowth processes.

In one embodiment of the invention, the augmentation means comprises a plurality of augmentation pieces of varying sizes and/or shapes, so as to allow the surgeon to select a piece which is most appropriate for filling the defect. This arrangement allows the surgeon some degree of flexibility in the operating theater to achieve a more precise fit, thus increasing the probability for the long-term success of the implant.

Other objects, advantages and novel features of the present invention will become apparent from the following detailed description of the invention when considered in conjunction with the accompanying drawings.

BRIEF DESCRIPTION OF THE DRAWINGS

FIG. 4 is a top view of a primary shell component of the hip prosthesis;

FIGS. 5(a)-5(d) are bottom, front and cross-sections respectively, of an augmentation component of the hip prosthesis;

DETAILED DESCRIPTION OF THE PREFERRED EMBODIMENTS

Figure 1:
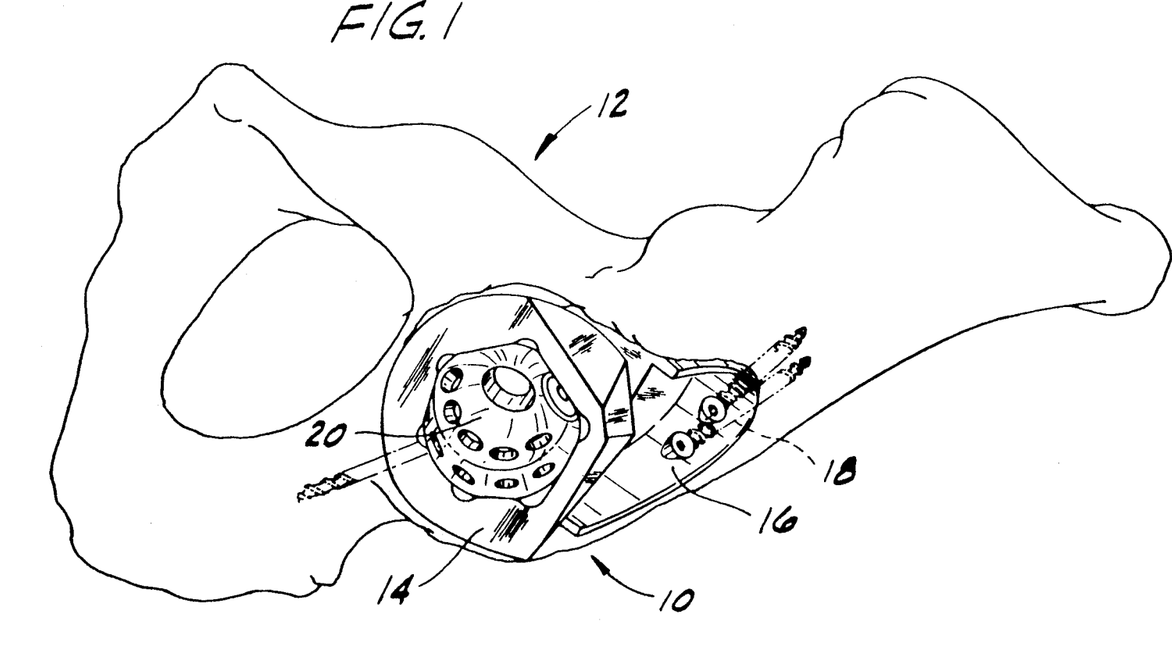
FIG. 1 is a schematic perspective of the hip prosthesis of the present invention shown as implanted in the acetabulum.

FIG. 1 schematically illustrates a hip prosthesis 10 which has been implanted into the acetabular region of a pelvic bone 12 of a patient. Prosthesis 10 comprises a primary acetabular shell 14 and an augmentation piece 16. Augmentation piece 16 is disposed within a void or defect, such as a rim or cavitary defect, located superiorly or posteriorly/superiorly to the anatomical center of rotation for the hip joint. Such a void or defect may have been caused, for example, by migration of a previously implanted device which, because of such migration and/or other complications, has been replaced by hip prosthesis 10. As will be described in connection with the drawings below, augmentation piece 16 may be fixed in a plurality of angular orientations, relative to shell 14, prior to being secured by bone screws 18 to the bony tissue of the ilium.

Primary shell 14 is provided with an internal cavity 20 which is adapted to receive a bearing insert (not shown) which, in turn, receives a femoral head portion of a femoral component of a total hip prosthesis (also not shown). Such bearing inserts are typically made of a plastic material, such as ultra high molecular weight polyethylene (UHMWPE).

Figure 2:
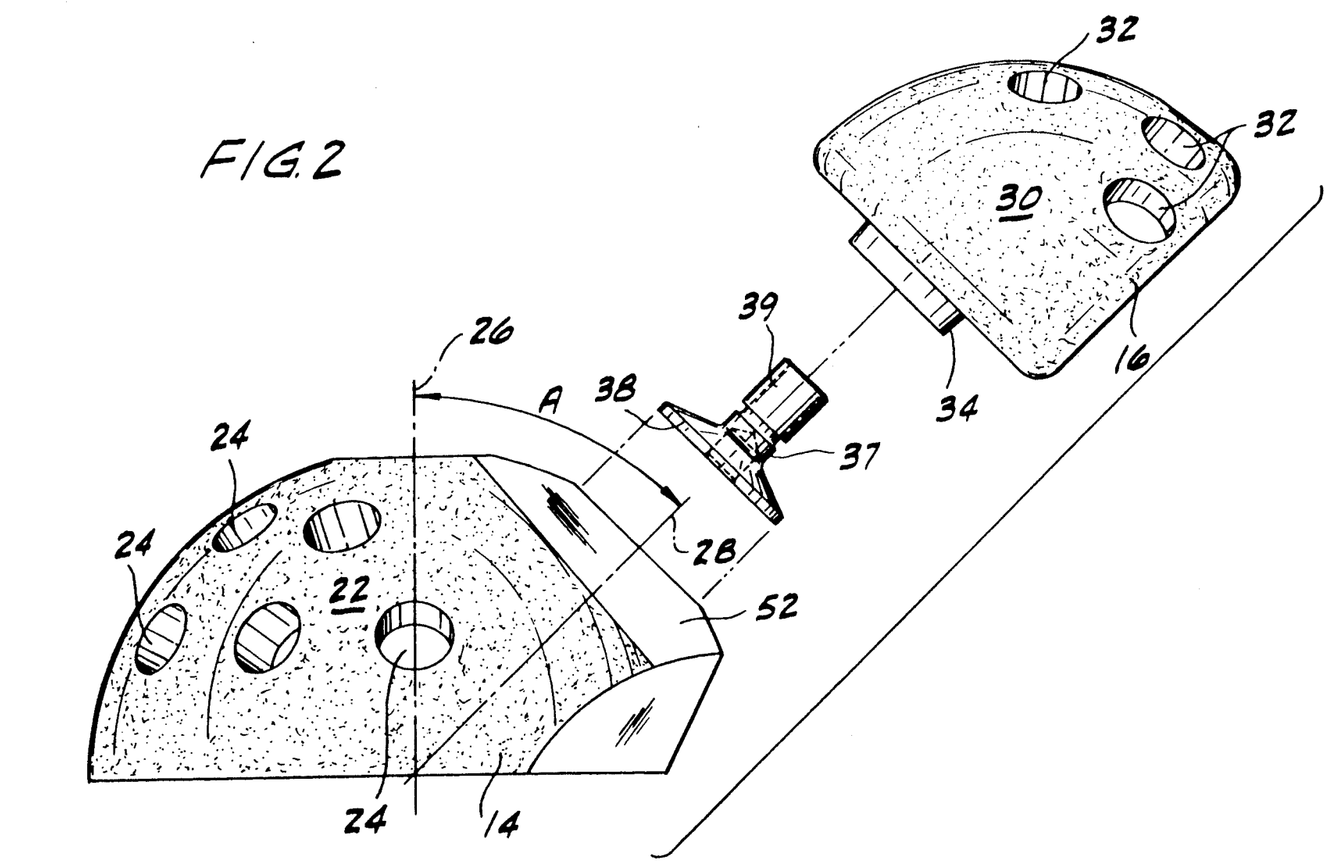
FIG. 2 is an exploded elevation of the hip prosthesis of the present invention.

FIG. 2 shows an exploded side view of the hip prosthesis 10 of the present invention. Primary shell 14 is substantially hemispherical in shape, and is provided with a porous metal coating on at least a portion of its outer surface 22 to promote bone ingrowth and long-term fixation. A plurality of holes 24 are also provided to accept one or more cancellous bone screws which are used to secure shell 14 to a surgically prepared acetabulem. Shell 14 has a polar axis 26 which extends through the approximate hemispherical center of the shell. Augmentation piece 16 is attached to shell 14 along another axis 28 which extends through the hemispherical center of shell 14 at an angle A, relative to axis 26. In the preferred embodiment of the invention illustrated, angle A is approximately 45°. Augmentation piece 16 is also provided with a porous metal coating on at least a portion of its outer surface 30, and is further provided with a plurality of holes 32 by which it is attached to surrounding bony tissue by one or more self-tapping cancellous bone screws 18.

Figure 3:
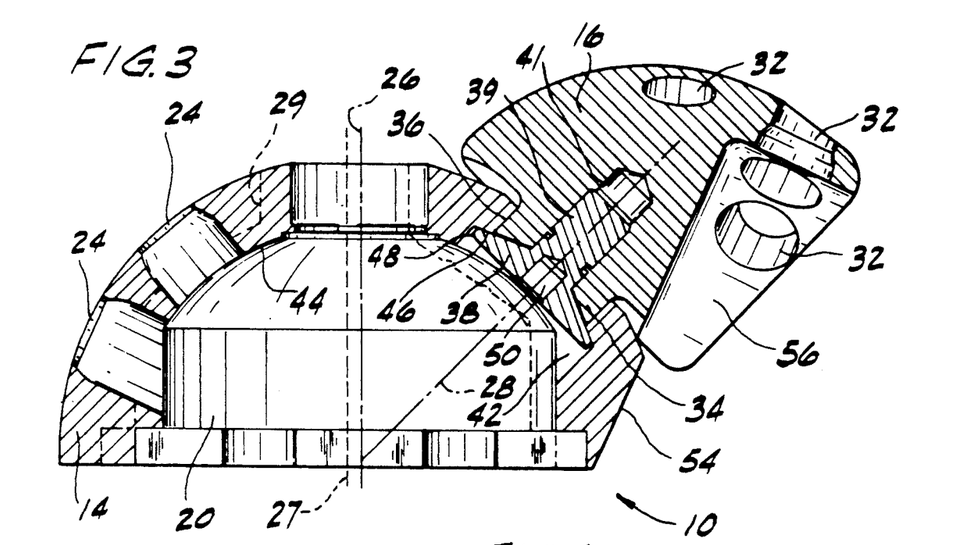
FIG. 3 is a cross-sectional of the hip prosthesis of FIG. 2 as assembled.
Figures 4, 5A:
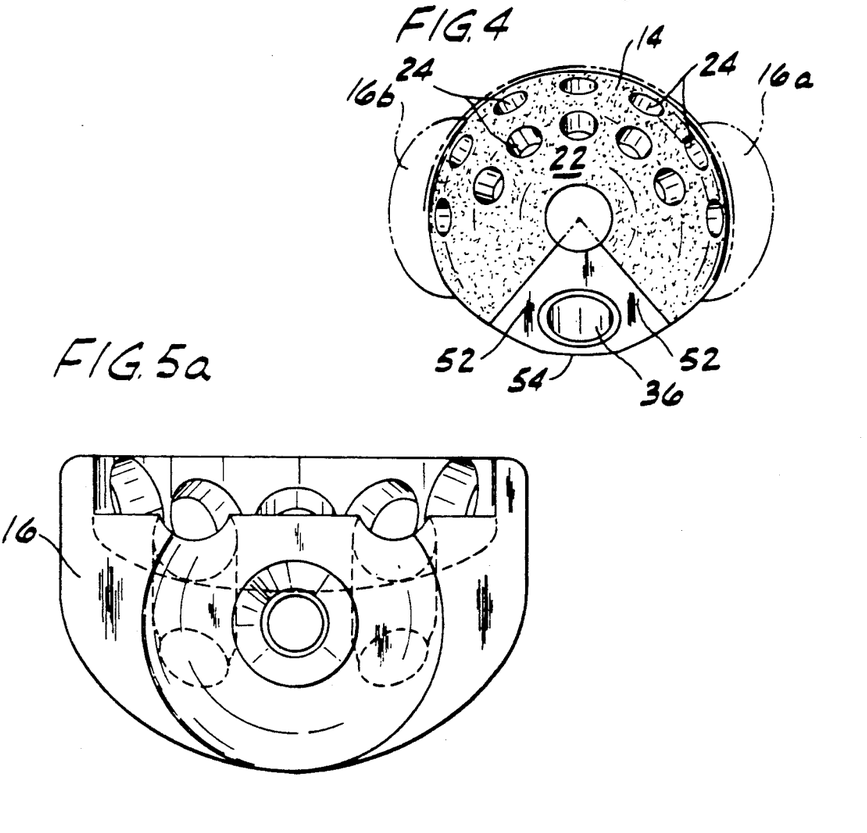
Figure 5B:
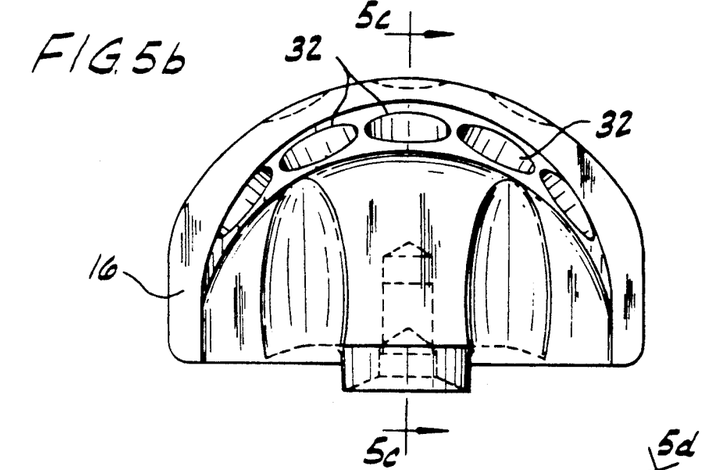
Figure 5C:
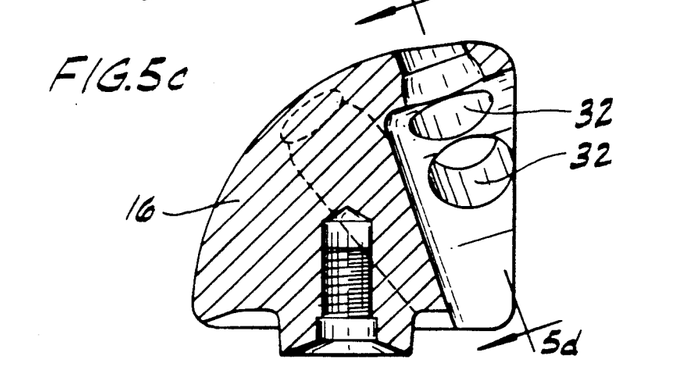
Figure 5D:
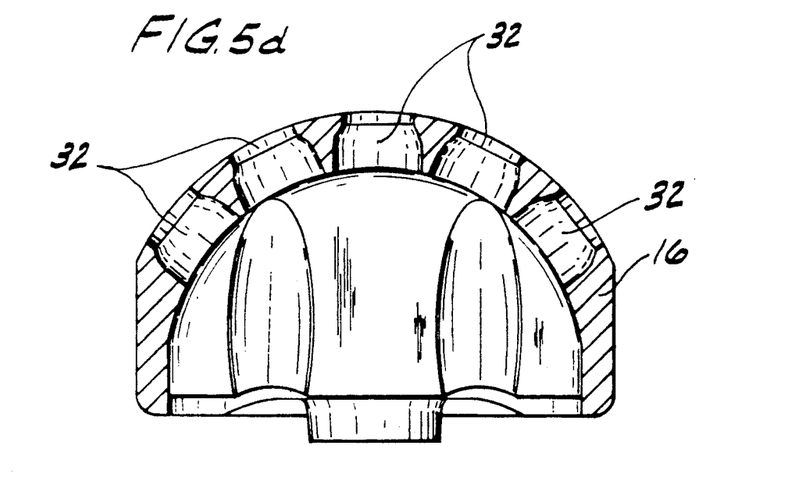

Augmentation piece 16 is attached to shell 14 by a morse taper arrangement which includes a tapered male projection 34 on augmentation piece 16, and a mating female opening 36 in primary shell 14 (FIGS. 3 and 4). This Morse type of arrangement constitutes the primary means of fixation between shell 14 and augmentation piece 16. The Morse taper arrangement allows augmentation piece 16 to be rotated about axis 28, relative to shell 14, as needed to fill the void or defect in the ilium, while allowing shell 14 to be located so as to re-establish, as nearly as possible, the original center of rotation for the hip joint. An additional advantage of allowing augmentation piece 16 to be rotated about axis 28 is that the same components (i.e., shell 14 and augmentation piece 16) can be used for both right and left hip joints. Assuming that the joints and defects in a particular patient were symmetrical in both hips, essentially identical implants, rotated by the same number of degrees in opposite directions, could be used. This feature reduces manufacturing and inventory costs which would otherwise be incurred if right-handed and left-handed devices were required.

Serving as a secondary means of fixation is machine screw 37 which is located along axis 28 as shown in FIGS. 2 and 3. Screw 37 has a broad head 38 and an elongate threaded portion 39. As shown in FIG. 3, threaded portion 39 extends into a threaded opening 41 within augmentation piece 16. Head 38, which is substantially wider than the diameter of the male Morse taper 34 which projects from augmentation piece 16, is received within a recess 42 formed in the inner wall 44 of cavity 20 of shell 14. A peripheral edge 46 of head 38 abuts a peripheral portion 48 of the bottom of recess 42 which surrounds the female Morse taper opening 36 so as to secure augmentation piece 16 firmly and fixedly to shell 14. A tool receiving opening 50 is provided in head 38 for purposes of allowing the prosthesis to be easily assembled.

As best illustrated in FIG. 2, portions of primary shell 14 have been trimmed away (such as at 52) to allow for unhampered rotation of augmentation piece 16. As is best illustrated in FIG. 3, a portion of primary shell 14 has also been trimmed away to create surface 54 to provide ready access to screw receiving openings 32 in augmentation piece 16 Augmentation piece 16 is further provided with a recess 56 to provide ready access (and approximately 10° of angulation) to screw receiving holes 32. Also shown in FIG. 3, in dashed lines, is an alternative central axis 27 and a dashed outline 29 to illustrate the possibility of shifting cavity 20 anteriorly, as viewed in FIG. 3, such that the hemispherical center of the shifted cavity is offset relative to the hemispherical center of shell 14. This arrangement will provide an increase in the thickness of the material available on the posterior side of shell 14, if necessary to accommodate fixation of augmentation piece 16. Offsetting cavity 20 will also allow for additional trimming to allow for further improvements and access to the bone screws which extend through holes 32.

FIG. 4 shows a top view of primary shell 14. FIG. 4 also shows, in dashed lines, additional augmentation pieces 16(a) and 16(b) which may be attached posteriorly and anteriorly, respectively to shell 14. One or the other of augmentation pieces 16(a) and 16(b) may be needed, in addition to augmentation piece 16, to more completely fill the acetabular defect.

FIGS. 5(a-d) show bottom, front, and cross-sectional views, respectfully, of augmentation piece 16. The embodiments illustrated in FIGS. 4 and 5(a-d) are considered to be representative of a plurality of such components which may differ in exact size and/or shape to provide the orthopedic surgeon with a number of options during the revision or reconstruction procedure. The "mating" elements of the components (i.e., Morse taper 34-36 and screw 37) remain substantially constant to allow the surgeon to mix and match components of varying sizes and shapes to suit the particular situation and defect as precisely as practical.

Figures 6A, 6B:
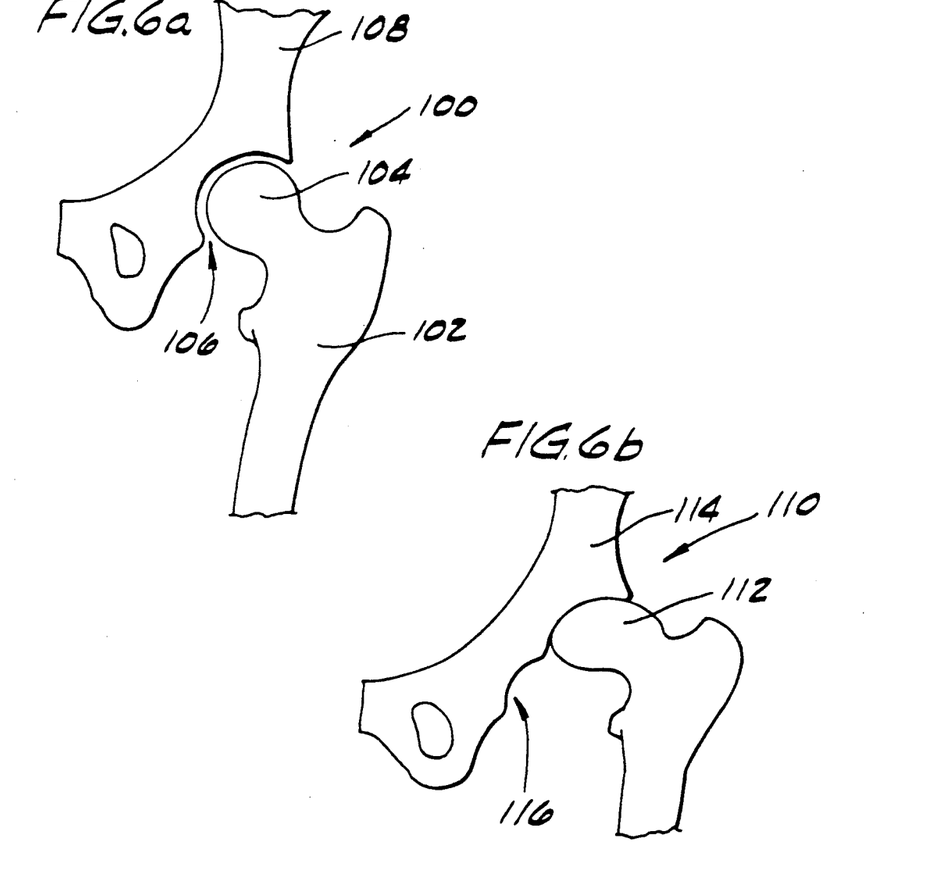
FIGS. 6(a)-6(c) illustrate a normal hip, and defects of the types to which the present invention may be applicable.

FIG. 6(a) schematically illustrates a normal hip joint 100 in which no defects are apparent. Hip joint 100 includes a femur 102 having a femoral head 104 which is received within the acetabulum 106 of pelvic bone 108.

FIG. 6(b) shows a hip joint 110 in which a defect has been caused by congenital dysplasia of the hip (CDH) with resultant arthritis. In joint 110, femoral head 112 has migrated superiorly into the region of pelvic bone 114 which lies above the natural acetabulum 116.

Figure 6C:
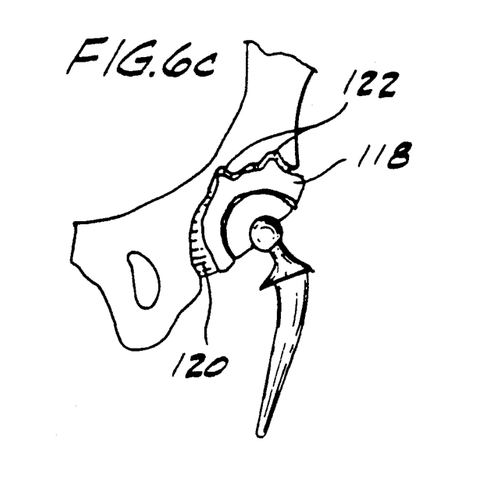

FIG. 6(c) illustrates a failed cemented acetabular component 118 of a total hip replacement. The cement has loosened from the bone and interposing fibrous scar tissue 120 is present between a portion of the acetabulum and component 118 Reaction to the loose component and cement has caused bone erosion to produce a superior acetabular defect, including localized cavitary defects 122, as illustrated.

Figure 7A:
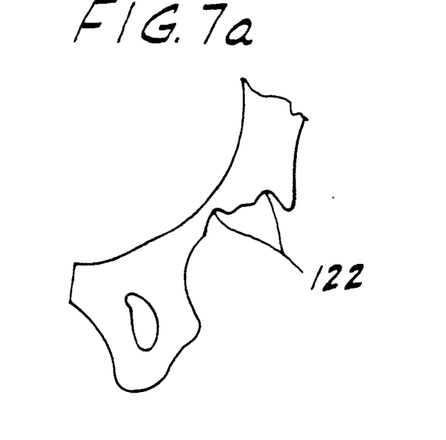
FIGS. 7(a)-7(j) illustrate a preferred manner of installing the hip prosthesis of the present invention.

FIGS. 7(a)-7(f) illustrate a preferred manner of installing the hip prosthesis of the present invention. FIG. 7(a) shows, for purposes of illustration, the pelvic bone of FIG. 6(c) after all loose components, cement, scar tissue and bone have been cleared away. The defect, which includes localized defects 122 and the general elongation of the acetabulum, are clearly apparent. At this point, the size, shape and location of the acetabular defect are assessed. A determination of bone quality (i.e., bone hardness) is also made.

Figure 7B:
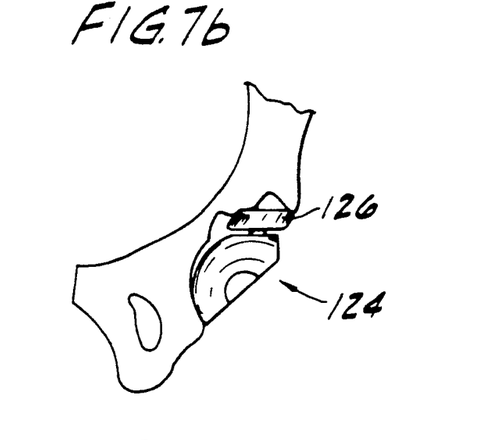

FIG. 7(b) illustrates the step of initially sizing the acetabulum with a plastic trial device 124. Several sizes of trial devices are available and, in general, the initial fitting will attempt to identify the largest plastic trial device that is deemed appropriate. This gives an indication of which reamer sizes should be used for preparing the acetabulum to receive the primary shell and augmentation piece. Initial fitting further gives some indication as to the approximate sizes of the implant components which should be used. The areas which will require reaming are also identified in this step. An initial determination as to the orientation of the augmentation piece (represented by trial device 126) is also apparent. The orientation of device 126 is typically superior or posterior/superior, relative to the natural acetabulum and the primary shell.

Figure 7C:
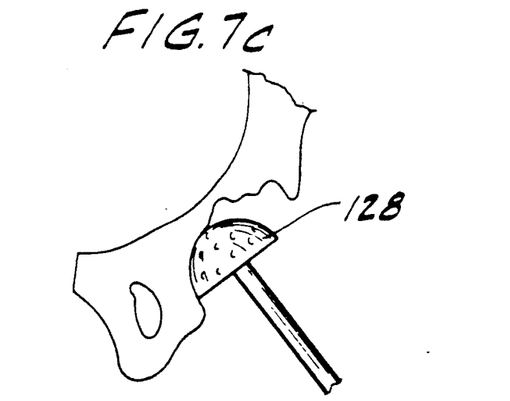

FIG. 7(c) illustrates the reaming of the lower acetabulum. A plurality of hemispherical reamers (represented in FIG. 7(c) by reamer 128) are available in incrementally increasing diameters for use in forming the lower portion of the acetabulum into a generally hemispherical shape. The limiting factor, in terms of reamer size, is the anterior and/or posterior acetabular wall thicknesses. Care must be taken so as not to overream the lower acetabulum and, thus, weaken the anterior or posterior walls unnecessarily.

Figure 7D:
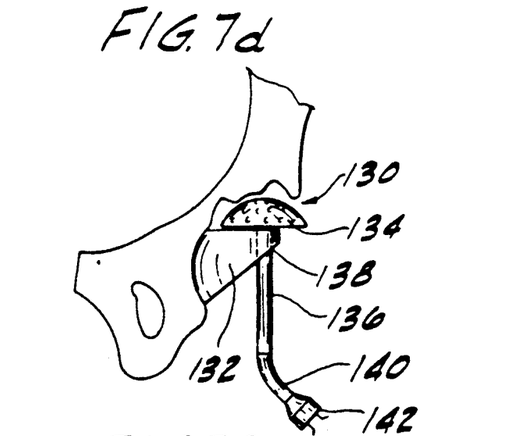

FIG. 7(d) illustrates the positioning of an acetabular defect reamer 130. Acetabular defect reamer 130 employs a reaming guide which includes positioning segment 132 which is slightly more than one quarter of a sphere (i.e., half a hemisphere), and is provided in incremental size diameters corresponding to the diameters of the reamers used to prepare the lower acetabulum. The particular positioning segment chosen generally corresponds to the last size reamer used on the lower acetabulum. The defect reamer portion has a relatively flat reamer head 134 which is attached to a rigid shaft 136. Shaft 136 is positioned in an opening 138 of positioning segment 132, and is thus guided thereby. Shaft 136 may be driven by a flexible drive shaft 140 which, in turn, is attached to drill head 142. The diameter of reamer head 134 is selected on the basis of the initial trial fitting described above in connection with FIG. 7(b). The diameters of reamer heads 134 which are available correspond to the diameters of the available augmentation components. Different size defect reamers are freely interchangeable with different size positioning segments.

Figure 7E:
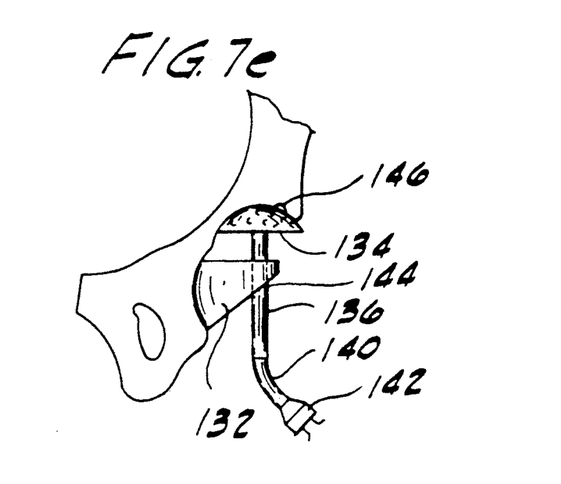

FIG. 7(e) illustrates the step of reaming the superior acetabular defect. As illustrated, drill head 142 turns reamer head 134 while manual pressure is applied to shape the defect to correspond with the selected augmentation piece. The depth of reaming must be balanced between creating a suitable bed for the augmentation piece and preservation of viable bone. The depth of reaming may be calibrated by markings 144 on shaft 136 and/or positioning segment 132 The calibration features of the reamer and positioning segment are illustrated in additional detail in FIG. 8. The calibration feature allows reaming to be controlled to a depth which will correspond to a selected augmentation piece.

As illustrated in FIG. 7(e), a small portion 146 of the defect has been left to preserve bone stock. This small defect will be filled with particulate bone graft prior to final implantation of the prosthesis.

Figure 7F:
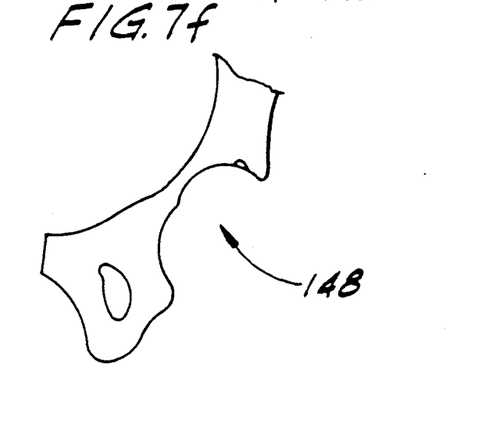

FIG. 7(f) shows the prepared acetabulum 148 following completion of the reaming process. It should be noted that the reaming process is controlled by several variables. For instance, the diameter of both the lower acetabulum and defect areas may be controlled by increasing the reamer diameter. The direction of defect reaming may also be varied, depending upon the exact location and orientation of the defect. For example, in the case of a posterior/superior defect, the reamer of FIG. 7(e) may be rotated posteriorly (i.e., into the page), whereas for a more superior defect, the reamer may be rotated superiorly (i.e., out of the page). The reamer may also be tilted clockwise (relative to the positioning shown in FIG. 7(e)) if it is desired to position the acetabulum in a more vertical orientation (abduction). Correspondingly, if less vertical orientation is desired, the reamer may be rotated in a clockwise direction, as viewed in FIG. 7(e). The relationship between orientation of the lower acetabular reamed area and the reamed area of the defect is controlled by fixing the axis of shaft 136 through the opening 138 in positioning segment 132. As noted, the depth of the reaming in the area of the defect corresponds to the height of the augmentation piece, and is controlled by the calibrated scale (137 in FIG. 8) on shaft 136 These control variables help assure correspondence between the geometry of the reamed acetabular portion of the joint, and the prosthetic components to be implanted.

Figure 7G:
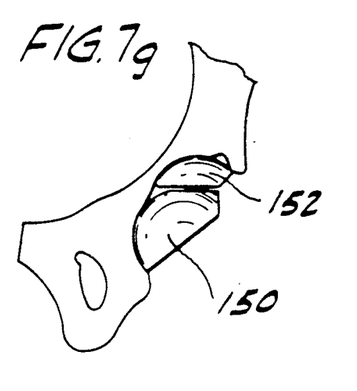
Figure 7H:
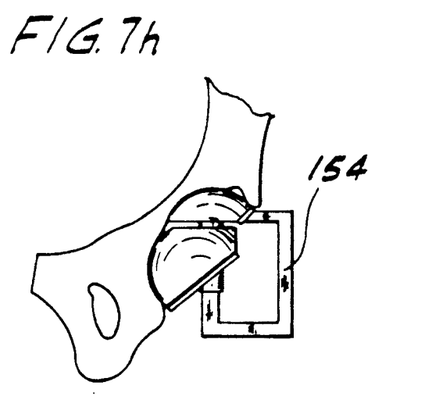
Figure 7I:
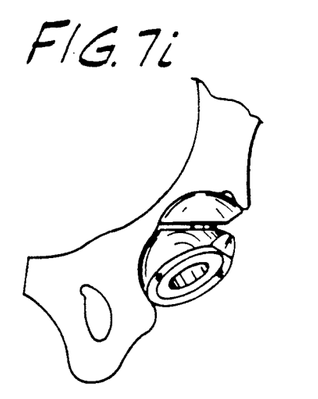

FIG. 7(g) illustrates the first step in final trial sizing. Various sizes of plastic trial devices are available. The appropriate diameter trial shell 150 is assembled with the appropriate diameter and height augmentation piece 152. These components are then positioned within prepared acetabulum 148, as shown in FIG. 7(g). After positioning, the fit is assessed. The primary shell is normally rotated forwardly (anteverted) to its final position, as shown in FIG. 7(i). An average degree of anteversion is 15°-20°. Anteversion is achieved by means of a measuring guide 154 which is shown in FIG. 7(h) and illustrated in detail in FIGS. 9(a) and 9(b).

Figures 8, 9A, 9B:
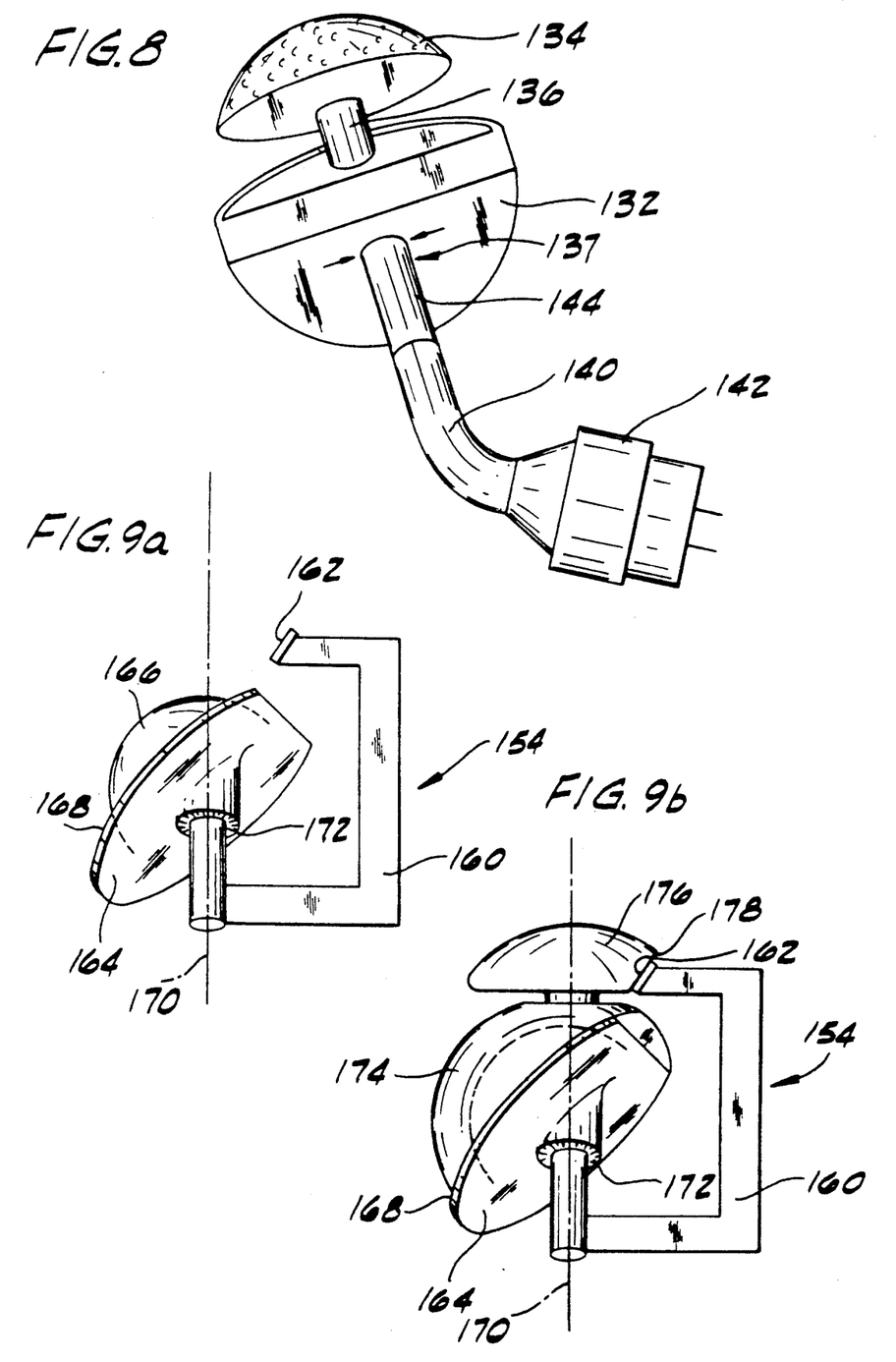
FIG. 8 shows an enlarged view of a defect reamer and positioning guide discussed in connection with FIGS. 7(d-e)
FIGS. 9(a) and 9(b) show a measuring guide used in installing the prosthesis of the present invention.

Measurement guide 154 is used to assemble the final components in the proper rotational orientation. Implant selection is based on the diameters and height of reaming and on bone quality. If the bone is dense and of good quality, implants may be selected which are two-four millimeters larger than the reamed acetabular cavity. Impaction of these "oversized" components create a tightly fitting implant. Weaker, softer bone may break if such a fit is attempted and may require oversizing by only one millimeter, or use of an implant which corresponds directly to the size of the reamed opening. The modularity of the prosthesis of the present invention allows individual decisions to be made for each portion of the prosthesis based on local bone quality, defect geometry, and other considerations.

Once the appropriate components of the implant are selected and assembled in the proper orientation using measuring guide 154, the implants are fixedly connected together, via the Morse taper and screw arrangement described above. The assembled prosthesis, including primary shell and augmentation piece, is then impacted into the prepared acetabulum. Implant positioning and stability is then assessed. If necessary, small amounts of bone grafts or hydroxyapatite particles are used to fill minor defects within the prepared acetabulum.

Figure 7J:
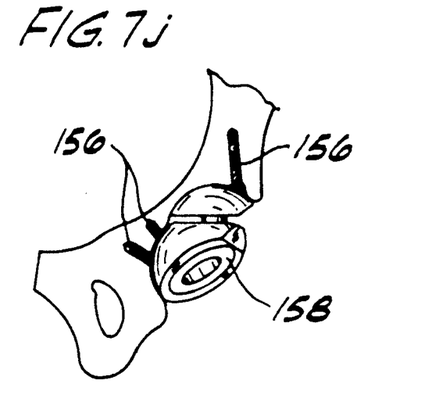

Following impaction of the prosthesis, fixation is enhanced through the use of self-tapping cancellous bone screws (156 in FIG. 7(j)) which extend through screw receiving openings in the primary shell and augmentation piece, as described previously. A polyethylene liner 158, with or without an elevated rim, is selected and inserted to complete the installation process.

FIG. 8 shows an inlarged view of the defect reamer and positioning guide discussed above in connection with FIGS. 7(a) and (e). Shown in FIG. 8 are positioning portion 132, reamer head 134, shaft 136, flexible drive shaft 140 and drill head portion 142. As discussed above, shaft 136 is calibrated (for example in the area generally indicated by reference numeral 137) to provide a means for precisely measuring the depth of reaming so as to avoid unnecessary removal of bone stock. The depth of reaming may be read directly by means of the numbering on shaft 136, and corresponds to the height of the augmentation piece which will subsequently be implanted.

FIG. 9(a) shows an enlarged, frontal view of measuring guide 154. Guide 154 includes a C-shaped arm 160 which includes a bearing surface 162 at the top-most portion of the "C". Supported on the lower arm of the "C" is an angled platform 164 which includes a dome-shaped protuberance 166 on an outwardly facing surface 168 thereof. Platform 164 is angularly adjustable about axis 170. A dial and appropriate markings are provided on surface 172 to measure the degrees of rotation between C-shaped portion 160 and platform 164. FIG. 9(b) shows measuring guide 154 with a primary shell 174 and augmentation piece 176 mounted thereon. Surface 162 abuts surface 178 of augmentation piece 176, as shown. Axis 170 extends coaxially with the axis which extends through the means for attaching augmentation piece 176 to primary shell 174 (e.g., axis 28 in FIG. 3). Accordingly, as platform 164 is rotated, relative to C-shaped portion 160, the angle of anteversion between the shell and augmentation piece can be precisely set.

From the preceding description of the preferred embodiments, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. An implantable hip prosthesis, comprising:
   a primary shell having an outer surface adapted to be received within a surgically prepared acetabulum, and having an inner cavity for receiving a bearing insert which, in turn, receives a femoral head portion of a femoral component of a total hip prosthesis;
   augmentation means sized for filling a superior or superior/posterior defect in the acetabulum; and
   an attachment member extending from the primary shell to said augmentation means for attaching said augmentation means to the primary shell.

2. A hip prosthesis according to claim 1, further comprising means for anchoring the augmentation mans to bony tissue surrounding the defect.

3. A hip prosthesis according to claim 2, wherein said means for anchoring the augmentation means comprises self-tapping bone screws.

4. A hip prosthesis according to claim 1, wherein at least one of a portion of the outer surface of the primary shell and a portion of an outer surface of the augmentation means are porous coated to promote fixation to the adjacent bone by bone ingrowth processes.

5. A hip prosthesis according to claim 1, wherein said augmentation means comprises a plurality of augmentation pieces of varying sizes, and means for attaching a selected one of said augmentation pieces to the primary shell to fill the defect.

6. A hip prosthesis according to claim 5, further comprising means for anchoring the selected augmentation piece to bony tissue in the superior or superior/posterior region of the ilium.

7. A hip prosthesis according to claim 6, wherein said means for anchoring the augmentation piece comprises self-tapping bone screws.

8. A hip prosthesis according to claim 1, wherein said primary shell is substantially hemispherical.

9. A hip prosthesis according to claim 8, wherein said inner cavity is substantially hemispherical in shape, and wherein a hemispherical center of the cavity is offset from a hemispherical center of the primary shell.

10. A hip prosthesis according to claim 9, wherein said cavity center is offset inferiorly, relative to said primary shell center.

11. A hip prosthesis according to claim 1, further comprising additional augmentation means, attachable to the primary shell, for filling at least one of a posterior defect and an anterior defect adjacent the surgically prepared acetabulum.

12. A hip prosthesis according to claim 1 wherein said augmentation means comprises an augmentation piece having a curved first surface adapted for reception in the acetabular defect for substantially filling the defect.

13. An implantable hip prosthesis, comprising:
a primary shell having an outer surface adapted to be received within a surgically prepared acetabulum, and having an inner cavity for receiving a bearing insert which, in turn, receives a femoral head portion of a femoral component of a total hip prosthesis; and
augmentation means, attachable to the primary shell, for filling a superior or superior/posterior defect in the acetabulum;
said augmentation means comprising an augmentation piece, means for attaching the augmentation piece to the primary shell so as to allow the augmentation piece to be angularly adjusted relative to the shell, and means for fixedly retaining the augmentation piece in a selected angular orientation.

14. A hip prosthesis according to claim 13, wherein said augmentation piece has a curved first surface adapted for implantation adjacent the bony tissue of the ilium, a second surface adapted for disposition adjacent the outer surface of the primary shell, and a third surface adapted for facing outwardly from the ilium when the hip prosthesis is positioned within the acetabulum.

15. A hip prosthesis according to claim 14, wherein said augmentation piece has a plurality of holes extending from said third surface to said first surface for receiving bone screws to anchor the augmentation piece to the surrounding bony tissue.

16. A hip prosthesis according to claim 15, wherein said third surface is provided with a recess to improve access to screws used to anchor the augmentation piece to the bony tissue of the ilium.

17. A hip prosthesis according to claim 13, wherein said means for attaching the augmentation piece to the primary shell and for fixedly retaining the augmentation piece in a selected angular orientation, comprise a Morse taper and screw means located along a common axis which extends through the primary shell and the augmentation piece.

18. A hip prosthesis according to claim 17, wherein said screw means has a body and a head, and wherein said screw head is received within a recess formed within the inner cavity of the primary shell, and the body is received within a threaded hole formed in the augmentation piece.

19. A hip prosthesis according to claim 17, wherein said common axis extends through the shell and the augmentation piece at an angle of approximately 45° relative to a polar axis of the shell.

20. An implantable hip prosthesis, comprising:
a primary shell having an outer surface adapted to be received within a surgically prepared acetabulum, and having an inner cavity for receiving a bearing insert which, in turn, receives a femoral head portion of a femoral component of a total hip prosthesis; and
augmentation means, attachable to the primary shell, for filling a superior or superior/posterior defect in the acetabulum;
said augmentation means comprising a plurality of augmentation pieces of varying sizes, and means for attaching a selected one of said augmentation pieces to the primary shell to fill the defect;
said means for attaching comprising means for allowing the augmentation piece to be angularly adjusted relative to the shell, and wherein said augmentation means further comprises means for fixedly retaining the augmentation piece in a selected angular orientation.

21. A hip prosthesis according to claim 20, wherein said selected augmentation piece has a curved first surface adapted for implantation adjacent the bony tissue of the surgically prepared defect, a second surface adapted for disposition adjacent the outer surface of the primary shell, and a third surface adapted for facing outwardly from the ilium when the hip prosthesis is positioned within the acetabulum.

22. A hip prosthesis according to claim 21, wherein said augmentation piece has a plurality of holes extending from said third surface to said first surface for receiving bone screws to anchor the augmentation piece to the surrounding bony tissue.

23. A hip prosthesis according to claim 22, wherein said third surface is provided with a recess to improve access to screws used to anchor the augmentation piece to the bony tissue of the ilium.

24. A hip prosthesis according to claim 20, wherein said means for attaching the augmentation piece to the primary shell and for fixedly retaining the augmentation piece in a selected angular orientation, comprise a Morse taper and screw means located along a common axis which extends through the primary shell and the augmentation piece.

25. A hip prosthesis according to claim 24 wherein said screw means has a body and a head, and wherein said screw head is received within a recess formed within the inner cavity of the primary shell, and the body is received within a threaded hole formed in the augmentation piece.

26. A hop prosthesis according to claim 24, wherein said common axis extends through the shell and the augmentation piece at an angle of approximately 45° relative to a polar axis of the shell.

* * * * *